United States Patent [19]
Yamauchi et al.

[11] Patent Number: 5,258,301
[45] Date of Patent: Nov. 2, 1993

[54] PROCESS FOR PRODUCING NUCLEOSIDES

[75] Inventors: Hiroshi Yamauchi, Toda; Hideki Utsugi; Yuichiro Midorikawa, both of Choshi, all of Japan

[73] Assignee: Yamasa Shoyu Kabushiki Kaisha, Chiba, Japan

[21] Appl. No.: 602,221

[22] PCT Filed: Feb. 27, 1990

[86] PCT No.: PCT/JP90/00240
§ 371 Date: Oct. 26, 1990
§ 102(e) Date: Oct. 26, 1990

[87] PCT Pub. No.: WO90/10080
PCT Pub. Date: Jul. 9, 1990

[30] Foreign Application Priority Data
Feb. 28, 1989 [JP] Japan ................... 1-48785
Aug. 4, 1989 [JP] Japan ................... 1-203556

[51] Int. Cl.$^5$ .................. C12R 1/07; C12P 19/38; C12N 1/20; C12N 9/12
[52] U.S. Cl. .................. 435/252.5; 435/87; 435/88; 435/193; 435/194; 435/252.31; 435/832
[58] Field of Search .............. 435/194, 832, 252.5, 435/193, 252.31, 87, 88

[56] References Cited

U.S. PATENT DOCUMENTS 4,331,762  5/1982  Nakajima et al. ................... 435/190

FOREIGN PATENT DOCUMENTS 56-148289  11/1981  Japan .

OTHER PUBLICATIONS

Chemical Abstracts, vol. 71, No. 13, Sep. 29, 1969, Columbus, Ohio, Abstract No. 56941r.

*Primary Examiner*—Herbert J. Lilling
*Attorney, Agent, or Firm*—Wenderoth, Lind & Ponack

[57] ABSTRACT

The present invention concerns a process for producing nucleosides by carrying out the reaction of a base donor, a saccharide residue donor and a phosphoric acid donor by the use of an enzyme preparation containing nucleoside phosphorylase, thereby forming an N-glycosidic bond between the base moiety of the base donor and the saccharide moiety of the saccharide residue donor, which comprises using, as the enzyme preparation containing nucleoside phosphorylase, a preparation derived from the cells of one or more kinds of microorganisms belonging to thermophiles of the genus Bacillus and having high nucleoside phosphorylase activity per unit cell weight.

1 Claim, 3 Drawing Sheets

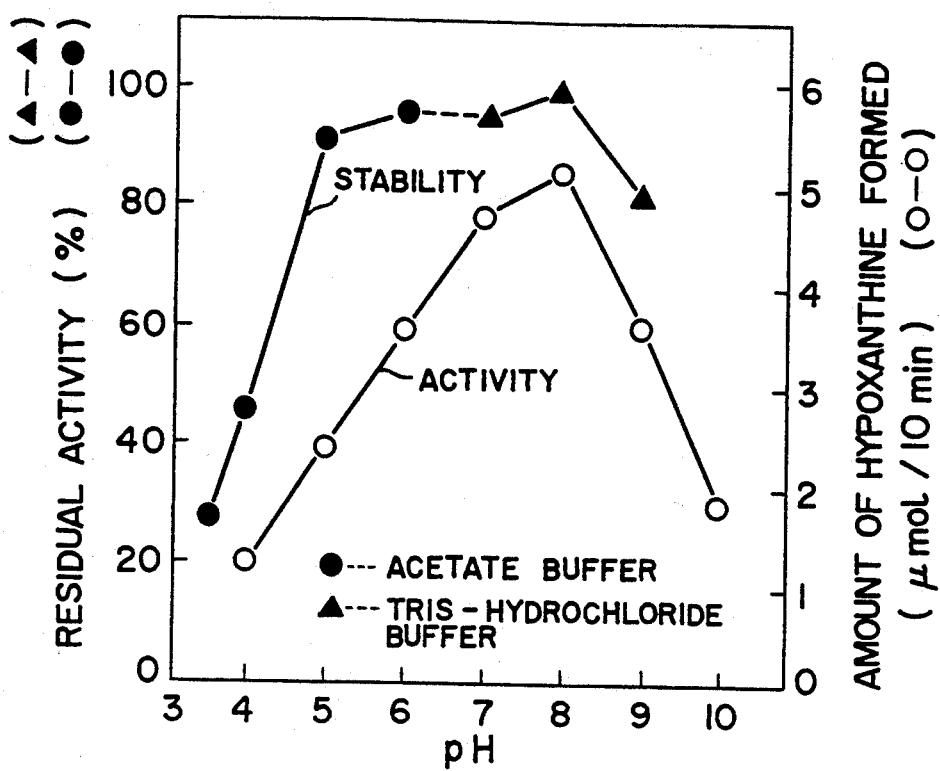
F I G. 1
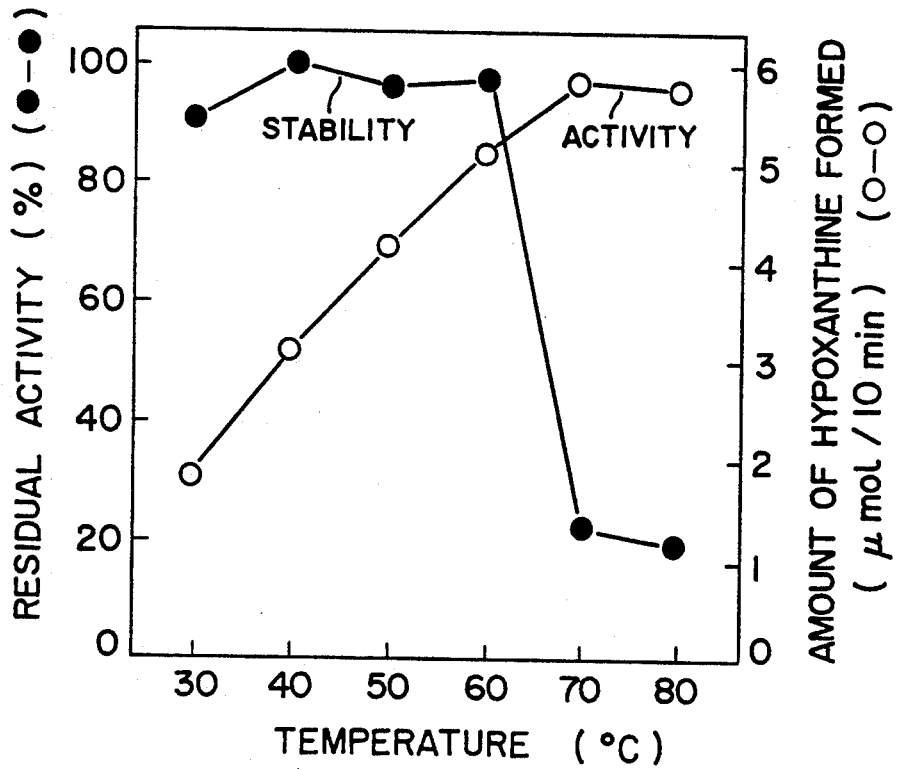
F I G. 2

PROCESS FOR PRODUCING NUCLEOSIDES

TECHNICAL FIELD

This invention relates to a process for producing nucleosides by the use of an enzyme preparation containing nucleoside phosphorylase derived from thermophiles belonging to the genus Bacillus.

BACKGROUND ART

As processes for producing nucleosides by reacting a saccharide residue donor such as nucleoside and ribose 1-phosphate enzymatically with a base donor, for example, there have been reported various processes for producing various purine nucleosides (Japanese Patent Publications Nos. 24475/1968, 28954/1968, 28955/1968, 28956/1968, 11116/1970, 14957/1973, Japanese Laid-Open Patent Publications Nos. 71495/1980, 18599/1981, 142293/1981, 164793/1981, 166199/1981, 63393/1983, 94396/1983, 170493/1983, etc.), processes for producing various pyrimidine nucleosides (Japanese Patent Publication No. 16478/1960, Japanese Laid-Open Patent Publications Nos. 102794/1981, 213397/1984, 239495/1985, etc.), and processes for producing other various nucleosides (Japanese Laid-Open Patent Publications Nos. 29720/1975, 146593/1982, 190396/1983, 216696/1983, 143599/1984, 179094/1984, 213397/1984, 120981/1985, 133896/1985, 31093/1988, 177797/1988, etc.).

However, although these enzymatic processes for production of nucleosides are excellent as compared with chemical synthetic methods with respect to substrate specificity and steric selectivity inherent in enzymatic reaction, the activity of the enzyme has not been sufficient, and they have not been found satisfactory with respect to yield in all cases.

Also, when the reaction is carried out at room temperature, lowering in yield which may be considered to be caused by contamination with bacteria is observed, and when the reaction is carried out at a higher temperature (e.g., 45° C. or higher) in order to avoid contamination, the enzyme gradually becomes deactivated, consequently leading to a marked lowering in yield.

Generally speaking, synthesis of a compound will be brought about by inclination of the equilibrium between the formation reaction and the decomposition reaction toward the formation reaction For this reason, for increasing the yield of the compound, it is important to promote the formation reaction and suppress the decomposition reaction, and this principle is not exceptional in the enzymatic process for the production of a compound.

Also, if the reaction temperature is made higher, the reaction rate will become more rapid, whereby the reaction will be completed within a shorter time and the solubility of the substrate will also be enhanced, and hence it has the possibility of producing the objective product with good yield.

When producing nucleosides by the use of nucleoside phosphorylase, for promoting the formation reaction of nucleosides, consideration must be taken from the two points of the activity of the enzyme itself to be used as a catalyst and the reaction conditions. Selection of the reaction conditions is no more than an auxiliary means for inducing the activity of the enzyme employed, and the drastic method for promoting the formation reaction to increase the yield of the objective compounds is to use nucleoside phosphorylase having excellent activity.

The nucleoside phosphorylases of the prior art which have been used in the production of nucleosides are for the most part those prepared from microorganisms which can be easily cultured. However, when the activity of the enzyme is examined from the efficiency of the reaction, specific activity, heat resistance, yield of the objective compound, etc., those which have been used in the prior art have not always been satisfactory.

On the other hand, concerning the enzyme which has been considered to participate in the decomposition reaction of the production of nucleosides, for example, nucleosidase, the method of inhibiting the nucleosidase by means of the immobilization method using a photocurable resin has been reported (Japanese Laid-Open Patent Publication No. 253393/1987). This method is excellent, but when using microorganism cells as an enzyme preparation, some microorganisms cannot be easily immobilized, thus the method lacks general purpose applicability.

The present inventors have screened various microorganisms in order to discover enzymes of excellent activity which can be used for enzymatic production of nucleosides and consequently discovered a group of microorganisms containing a large amount of heat-resistant nucleoside phosphorylase having extremely high specific activity, and having high nucleoside phosphorylase activity per unit cell weight among thermophiles belonging to the genus Bacillus.

In the prior art, nucleoside phosphorylase has been isolated and purified from *Bacillus stearothermophilus* which is a thermophile belonging to the genus Bacillus and the enzymatic properties of the enzyme have been reported (see J. Biol. Chem., 244, 3691-3697 (1969), Agric. Biol. Chem., 53, 2205-2210 (Aug. 23, 1989), Agric. Biol Chem., 53, 3219-3224 (Dec. 23, 1989)). Also, a process for producing 5-methyluridine or thymidine by using microorganism cells of *Bacillus stearothermophilus* as an enzyme source has been reported (see Japanese Laid-Open Patent Publication No. 320995/1989 (published on Dec. 27, 1989), Agric. Biol. Chem., 53, 197-202 (Jan. 23, 1989)). However, the nucleoside phosphorylases of the above-mentioned reports, although having the advantage of heat resistance, have low specific activity and also low enzyme activity per unit cell weight and thus could not solve the problem of the prior art that no nucleoside can be efficiently produced More specifically, when the yield of the nucleoside disclosed in Japanese Laid-Open Patent Publication No. 320995/1989 is represented in terms of its proportion relative to the base donor employed, it is at most around 30% (even if the reaction has occurred ideally, the yield of the objective product determined from the equilibrium constant of the enzyme reaction is 53 to 56%).

DISCLOSURE OF THE INVENTION

The present inventors have further studied the group of microorganisms found by the present inventors as mentioned above, containing a large amount of heat-resistant nucleoside phosphorylase having high specific activity, and having high nucleoside phosphorylase activity per unit cell weight, and consequently found that (1) the group of these microorganisms, while having both purine nucleoside phosphorylase and pyrimidine nucleoside phosphorylase having heat resistance and high specific activity in combination, contains no nucleosidase, or if any, exhibits very weak activity at the reaction temperature during the production of nucleosides (35° to 80° C.), and that (2) by the use of the enzyme preparation containing the nucleoside phosphorylase derived from the cells of one or more kinds of the microorganisms in the enzymatic production of nucleosides, the objective nucleosides can be produced with good yield within a short time only by a small amount of the enzyme, whereby the present invention has been accomplished.

More specifically, the present invention concerns, in a process for producing nucleosides by carrying out the reaction of a base donor, a saccharide residue donor and a phosphoric acid donor by the use of an enzyme preparation containing nucleoside phosphorylase, thereby forming an N-glycosidic bond between the base moiety of the base donor and the saccharide moiety of the saccharide residue donor, the improvement which comprises using, as the enzyme preparation containing nucleoside phosphorylase, a preparation derived from the cells of one or more kinds of microorganisms belonging to thermophiles of the genus Bacillus and having high nucleoside phosphorylase activity per unit cell weight.

In the present specification, "nucleosides" refer to nucleosides existing in nature such as uridine, thymidine, cytidine, adenosine and guanosine, and also include various nucleoside analogs.

Also, the present invention concerns the above-mentioned enzyme preparation itself, the novel microorganism to be used for preparation of said enzyme preparation, and the novel nucleoside phosphorylase prepared from said microorganism which can be used for the production of nucleosides.

BRIEF DESCRIPTION OF THE DRAWINGS

FIG. 1 is a graph indicating the optimum pH and the stable pH range of the purine nucleoside phosphorylase of the present invention.

FIG. 2 is a graph indicating the optimum temperature and the stable temperature range of the purine nucleoside phosphorylase of the present invention.

BEST MODE FOR PRACTICING THE INVENTION

Enzyme preparation containing nucleoside phosphorylase

Figure 3:
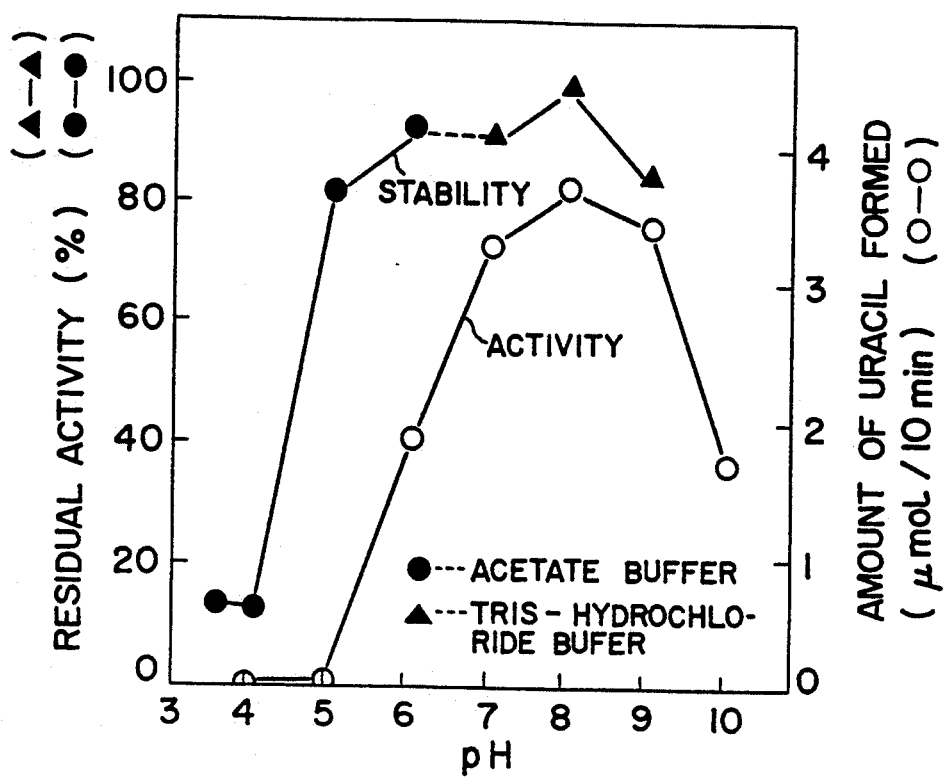
FIG. 3 is a graph indicating the optimum pH and the stable pH range of the pyrimidine nucleoside phosphorylase of the present invention.

The "enzyme preparation containing nucleoside phosphorylase" of the present invention (hereinafter called "enzyme preparation") refers to a preparation containing at least one, preferably both, of purine nucleoside phosphorylase and pyrimidine nucleoside phosphorylase.

The "degree of enzyme purity" means the proportion of the enzyme protein amount in the total protein amount.

The enzyme preparation of the present invention can be prepared from the microorganisms having high nucleoside phosphorylase activity per unit cell weight (hereinafter called "the microorganisms of the present invention") among the microorganisms belonging to thermophiles belonging to the genus Bacillus, specifically moderate thermophiles such as *Bacillus acidocaldarius, Bacillus schlegeli* and *Bacillus stearothermophilus.*

As nucleoside phosphorylase activities for selection of the microorganisms, for example, the following values may be mentioned as a measure:

purine nucleoside phosphorylase
  10 or more U/g-wet cells, preferably 12 or more U/g-wet cells pyrimidine nucleoside phosphorylase
  10 or more U/g-wet cells, preferably 15 or more U/g-wet cells The microorganism which satisfies one of these two conditions can be used as a preparation source for the enzyme preparation to be used in the process of the present invention, and the microorganism which satisfies the above two conditions at the same time is preferable as a preparation source for the enzyme preparation.

Specific examples of preferable microorganisms satisfying such conditions are *Bacillus stearothermophilus* TH6-2, P-21, P-23, etc. (all are strains isolated from soil on the grounds of Yamasa Shoyu K.K.). The bacteriological characteristics of the TH6-2 strain which is the most representative among such strain group are shown below.

Bacteriological Characteristics of TH6-2

(A) Morphological Characteristics (1) Shape and size of cell: Short rod, 0.6–1.1×2–7 μm
(2) Formation of spores: Positive
(3) Swelling of sporangium: Positive
(4) Site and size of spores within cell: At the terminal or the center; 0.8×0.8–1.0 μm
(5) Gram staining: Gram variable (Gram-positive in the initial stage of cultivation)

(B) Cultural Characteristics on Various Culture Media (1) Broth agar (Bouillon-agar) slant medium: Abundant growth, smooth surface, opaque, no medium change
(2) Broth agar (Bouillon-agar) plate medium: Circular colony formation, thinly spread, exhibiting viscous property, opaque, wavy at the brim
(3) Litmus-milk medium: No growth (C) Physiological Properties (1) Growth in the presence of oxygen: Grown
(2) Growth in the absence of oxygen: Not grown
(3) Catalase: Positive
(4) V-P test: Negative
(5) Methyl red test (pH in V-P broth): <pH 6
(6) Hydrolysis:
Casein: Negative
Gelatin: Positive
Starch: Positive
(7) Utilization of citric acid: Positive
(8) Reduction of nitrate: Positive
(9) Formation of indole: Negative
(10) Requirement of sodium chloride or potassium chloride: Negative
(11) Formation of acids from saccharides:
Positive glucose, arabinose, xylose, fructose, maltose Negative: starch, glycerol, sucrose, raffinose
(12) Growth at respective pH's:
Grown at pH 6.8, not at pH 5.7
(13) Growth in the presence of sodium chloride
in the presence of 2% NaCl: Grown
in the presence of 5% NaCl: Not grown
(14) Growth range:
Growth pH range: 6.5 to 9.0
Growth temperature range: 35° to 65° C.
(15) Growth in the presence of glucose:
Not grown in the presence of 0.5% or more of glucose By referring these bacteriological characteristics to the classification standards of Bergey's Manual of Systematic Bacteriology (Eighth Edition), the above microorganism was found to belong to *Bacillus stearothermophilus* and designated as *Bacillus stearothermophilus* TH6-2. P-21 and P-23 were also found to exhibit the same bacteriological characteristics. TH6-2 has been deposited with the Fermentation Research Institute, Agency of Industrial Science and Technology 1-3, Higashi 1-chome, Tsukuba-shi, Ibaraki-ken 305, Japan in conformity with the Budapest treaty, and has been given FERM BP-2758 as the deposition number. This international deposition was based on the transference made on Feb. 16, 1990 from FERM P-10526 deposited domestically at the above depository on Feb. 4, 1989.

TH6-2, P-21 and P-23 all belong to *Bacillus stearothermophilus*, and can be distinguished clearly from known microorganisms in having very high nucleoside phosphorylase activity per unit cell weight and containing substantially no nucleosidase. For example, the comparison test of pyrimidine nucleoside phosphorylase and purine nucleoside phosphorylase activities per unit cell weight among known *Bacillus stearothermophilus* microorganisms stored at American Type Culture Collection (ATCC) and the above microorganisms of the present invention gave the results as shown in Table 1. From Table 1, it can be seen that the nucleoside phosphorylase activities per unit cell weight of TH6-2, P-21 and P-23 are all higher by a little less than 2-fold for purine nucleoside phosphorylase activity and by a little more than 6-fold for pyrimidine nucleoside phosphorylase activity as compared with the enzyme activities exhibited by the strains known in the art. Specifically, the present microorganisms were found to exhibit purine nucleoside phosphorylase activity and pyrimidine nucleoside phosphorylase activity per unit cell weight of 13–15 U/g-wet cells and 20–22 U/g-wet cells, respectively.

TABLE 1

| Microorganism | Purine Nucleoside Phosphorylase Activity (U/g-wet cells) | Pyrimidine Nucleoside Phosphorylase Activity (U/g-wet cells) |
| --- | --- | --- |
| Microorganisms of the present invention | | |
| (TH-6-2) | 14.2 | 2.8 |
| (P-21) | 13.9 | 21.8 |
| (P-23) | 13.4 | 21.4 |
| ATCC 8005 | 2.3 | 1.4 |
| ATCC 10149 | 5.4 | 0.8 |
| ATCC 12016 | 2.6 | 1.4 |
| ATCC 12976 | 2.3 | 0.4 |
| ATCC 12978 | 2.8 | 0.8 |
| ATCC 12980 | 4.5 | 0.4 |
| ATCC 15952 | 1.2 | 0.8 |
| ATCC 21365 | 8.7 | 3.4 |

TABLE 1-continued

| Microorganism | Purine Nucleoside Phosphorylase Activity (U/g-wet cells) | Pyrimidine Nucleoside Phosphorylase Activity (U/g-wet cells) |
| --- | --- | --- |
| ATCC 29609 | 3.4 | 0.4 |

Thus, the microorganisms of the present invention were found to sufficiently satisfy the selection standards of nucleoside phosphorylase activity as described above and to be useful as a preparation source of the enzyme preparation to be used for the production of nucleosides.

For verifying this fact, ribavirin was produced and the formation ratio of the objective compound was compared among the present microorganisms and known strains. As a result, as shown in Table 2, while formation ratios were 90% or more when all of the microorganisms of the present invention were employed, the formation ratio of known microorganisms was only 40% at the highest, whereby it was confirmed that the microorganisms of the present invention are extremely useful as an enzyme source for the production of nucleosides.

TABLE 2

| Microorganism | Formation Ratio of Ribavirin (%) <Ratio Relative to 1,2,4-Triazole-3-Carboxamide> |
| --- | --- |
| Microorganisms of the present invention | |
| (TH-6-2) | 95.0 |
| (P-21) | 95.0 |
| (P-23) | 94.1 |
| ATCC 7953 | 3.8 |
| ATCC 8005 | 30.3 |
| ATCC 10149 | 11.7 |
| ATCC 12016 | 44.4 |
| ATCC 12976 | 8.0 |
| ATCC 12978 | 43.5 |
| ATCC 12980 | 0 |
| ATCC 15952 | 39.0 |
| ATCC 21365 | 37.6 |
| ATCC 29609 | 4.1 |

In the comparison test as described above, the cells of microorganisms were prepared in the same manner as in Example 1 described below, and purine nucleoside phosphorylase activity and pyrimidine nucleoside phosphorylase activity were assayed according to the methods as also described below. On the other hand, ribavirin was produced by adding 10 ml of a suspension of microorganisms with equal cell weight (containing 200 mg as wet cells) to 10 ml of a substrate solution (aqueous solution of pH 6.0 containing 40 mM 1, 2, 4-triazole-3-carboxamide, 60 mM uridine, 40 mM potassium dihydrogenphosphate) and stirring the mixture of 50° C. for 24 hours. After the above reaction, the reaction mixture was centrifuged, the supernatant was diluted to 50 to 100-fold, and this was subjected to the HPLC method (column: YMC A-312 (manufactured by Yamamura Kagaku Kenkyusho, K.K.), eluent: 0.15M potassium dihydrogenphosphate solution, detection: absorbance at 220 nm) for the measurement of the amount of ribavirin formed.

The formation ratio was determined from the following formula:

$$\text{Formation ratio (\%)} = \frac{\text{Concentration of ribavirin formed (M)}}{\text{Concentration of 1,2,4-triazole-3-carboxamide used (M)}} \times 100$$

The enzyme preparation of the present invention can be prepared by culturing a microorganism belonging to the microorganism group of the present invention and suitably processing the microorganism cells obtained by the cultivation according to a use mode corresponding to use purpose.

As a medium for culturing the microorganism, those containing appropriate amounts of carbon sources and nitrogen sources assimilable by the microorganism, and containing also, if necessary, metal salts, trace amount growth promoting substances, defoaming agents, etc. added therein are employed. More specifically, examples of the medium components are saccharides (glucose, saccharose, etc.), natural carbohydrates (molasses, waste molasses, starch, wheat, bran, rice, etc.), alcohols, fatty acids, hydrocarbons, etc., and as nitrogen sources, meat extract, yeast extract, soybean hydrolyzate, Casamino acid, various amino acids, urea, etc., as inorganic salts, phosphates, hydrochlorides and sulfates of metals such as zinc, iron, magnesium, sodium, calcium, potassium, etc., and as trace amount growth promoting substances, vitamin $B_1$, vitamin $B_2$, pantothenic acid, and biotin.

Cultivation is carried out according to a conventional liquid culture method (shaking culture, aeration stirring culture, stationary culture, continuous culture, etc.)

The culture conditions depend on the microorganism and the culture medium employed, and thus cannot be specified. Generally, the pH at the initiation of culture is adjusted to 6.5 to 9.0, and cultivation is carried out until the desired enzyme activity can be amply obtained under the temperature condition of about 35° to 65° C., specifically for about 5 to 50 hours.

The mode of the enzyme preparation prepared by the use of the culture broth containing viable microorganisms thus obtained (hereinafter called cultured product) is not particularly limited, but, for example, the cultured product itself of the microorganisms, the viable microorganism cells separated from the cultured product by a conventional separation method (centrifugation, precipitation, agglutination, washing, etc.), or the treated product of the cells may be mentioned.

Further specific examples of the treated product of viable cells are the destroyed products of viable cells and the viable organisms with the cell walls and/or the cell membranes having been denatured obtained by treatment of the viable cells by the treatment methods used in general such as mechanical destruction (by Waring blender, French press, homogenizer, crucible, etc.), freezing and thawing, drying (freeze drying, air drying, acetone drying, etc.), autolysis (by solvent treatment with toluene, ethyl acetate, etc.), enzyme treatment (by cell wall dissolving enzyme such as lysozyme), sonication, osmotic pressure shock and chemical treatment (with solution of salts, acidic solution, alkaline solution, surfactant, chelating agent, etc.); or crude enzyme or purified enzyme obtained by fractionating the fractions having enzyme activity and further treating the extracted fractions, if necessary, according to the general enzyme purification methods (salting out, isoelectric point precipitation, organic solvent precipitation, various chromatographies, dialysis) to fractionate the fractions having the desired enzyme activity of the present invention.

Such a cultured product, viable microorganism cells and treated product may be used in the free state without applying immobilization treatment thereto, or may be used as an immobilized product obtained by an immobilization treatment such as entrapping, crosslinking or adsorption.

A specific example of the purified enzyme which is one form of the treated product of cells is the nucleoside phosphorylase obtained by extraction/purification from *Bacillus stearothermophilus* TH6-2 belonging to the microorganism group of the present invention having enzymological properties as described below.

(A) Purine Nucleoside Phosphorylase (1) Action

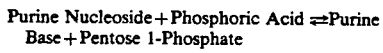

Purine Nucleoside + Phosphoric Acid ⇌ Purine Base + Pentose 1-Phosphate

The purine nucleoside phosphorylase of the present invention catalyzes the above phosphorolysis. For this reason, it belongs to the International Enzyme Classification E.C.2.4.2.1.

(2) Substrate specificity

The results of phosphorolysis of various purine nucleoside substrates are shown in Table 3.

TABLE 3

| Substrate | Amount of Base Formed (μmol 10 min.) | Relative Activity (%) |
|---|---|---|
| Adenosine | 0.15 | 5 |
| 2'-Deoxyadenosine | 0 | 0 |
| 3'-Deoxyadenosine | 0 | 0 |
| Arabinofuranosyl adenine | 0 | 0 |
| Inosine | 2.55 | 100 |
| 2'-Deoxyinosine | 2.54 | 100 |
| 3'-Deoxyinosine | 0 | 0 |
| Guanosine | 2.15 | 84 |
| 2'-Deoxyguanosine | 2.18 | 85 |

From Table 3, it can be seen that the purine nucleoside phosphorylase of the present invention is specific for inosine, 2'-deoxyinosine, guanosine and 2'-deoxyguanosine within the range tested.

(3) Optimum pH and pH stability

The optimum pH is pH 7 to 8, and the stable pH range is pH 5 to 9 (see FIG. 1).

(4) Optimum temperature and temperature stability

The optimum temperature is 60° to 80° C., and the stable temperature range is up to 60° C. (see FIG. 2).

(5) Molecular weight

The molecular weight measured by SDS-polyacrylamide gel electrophoresis is about 31,000.

(6) Titre (specific activity)

At 80% of enzyme purity, the specific activity of 400 or more (U/mg) is exhibited, and at 90% of enzyme purity, 450 (U/mg).

(B) Pyrimidine Nucleoside Phosphorylase (1) Action

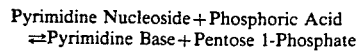

Pyrimidine Nucleoside + Phosphoric Acid ⇌ Pyrimidine Base + Pentose 1-Phosphate

The pyrimidine nucleoside phosphorylase of the present invention catalyzes the above phosphorolysis. For this reason, it belongs to the International Enzyme Classification E.C.2.4.2.2.

(2) Substrate specificity

The results of phosphorolysis of various pyrimidine nucleoside substrates are shown in Table 4.

TABLE 4

| Substrate | Amount of Base Formed (μmol/10 min.) | Relative Activity (%) |
|---|---|---|
| Uridine | 1.73 | 68 |
| 2'-Deoxyuridine | 2.55 | 100 |
| Arabinofuranosyl uracil | 0 | 0 |
| Pseudouridine | 0 | 0 |
| Cyclouridine | 0 | 0 |
| Cytidine | 0 | 0 |
| 2'-Deoxycytidine | 0 | 0 |
| Ribofuranosyl thymine | 0.96 | 38 |
| Thymidine | 1.71 | 67 |

From Table 4, it can be seen that the pyrimidine nucleoside phosphorylase of the present invention is specific for uridine, 2'-deoxyuridine, ribofuranosyl thymine, thymidine within the range tested.

(3) Optimum pH and pH stability

The optimum pH is pH 7 to 9, and the stable pH range is pH 5 to 9 (see FIG. 3).

(4) Optimum temperature and temperature stability

Figure 4:
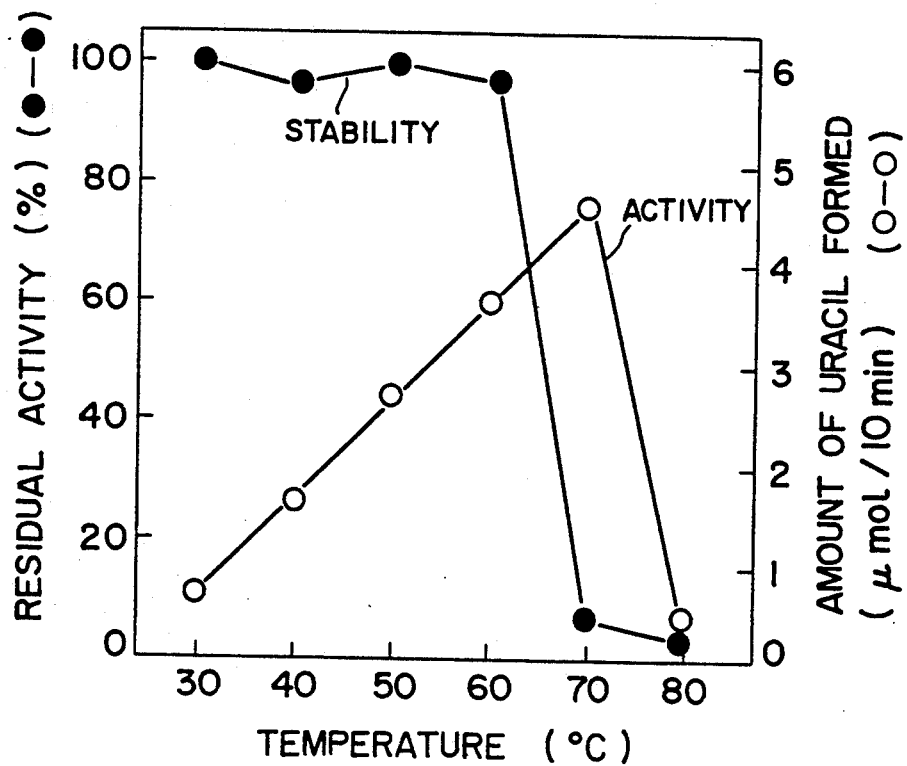
FIG. 4 is a graph indicating the optimum temperature and the stable temperature range of the pyrimidine nucleoside phosphorylase of the present invention.

The optimum temperature is 60° to 70° C., and the stable temperature range is up to 60° C. (see FIG. 4).

(5) Molecular weight

The molecular weight measured by SDS-polyacrylamide gel electrophoresis is about 45,000.

(6) Titre (specific activity)

At 80% of enzyme purity, the specific activity of 250 or more (U/mg) is exhibited, and at 90% of enzyme purity, 297 (U/mg).

The above enzymatic properties were assayed according to the methods described below.

1. Assay of Activity

Purine Nucleoside Phosphorylase Activity

Into 1.0 ml of a substrate solution (aqueous solution of pH 8.0 containing 20 mM inosine and 0.1M potassium dihydrogenphosphate) is added 20 μl of an enzyme solution (50 mM acetate buffer (pH 6.0) containing 1 μg of purified enzyme), and the reaction is carried out at 50° C. for 10 minutes. Then the reaction is stopped by addition of HCl to a final concentration of 0.1N, and also cooling at 0° C. for 10 minutes. Next, the reaction is subjected to centrifugation, and the supernatant obtained is then subjected to the HPLC method (column: YMC A-312 (manufactured by Yamamura Kagaku Kenkyusho, K.K.), eluent: 20 mM Tris-HCl buffer (pH 7.5) containing 5.0% acetonitrile, detection: 260 nm) to quantitate the hypoxanthine formed. The enzyme amount forming 1 μmol of hypoxanthine per one minute is defined as one unit ("U").

Pyrimidine Nucleoside Phosphorylase Activity

Except for using uridine in place of inosine in the substrate solution and quantitating uracil according to the HPLC method, the same method as in the above-described assay of purine nucleoside phosphorylase activity is conducted. The amount of enzyme forming 1 μmol of uracil per one minute is defined as one unit.

2. Substrate Specificity

By the use of an aqueous solution of pH 8.0 containing 10 mM of a nucleoside and 50 mM of potassium dihydrogenphosphate as a substrate solution, the reaction is carried out at 50° C. for 10 minutes, and after the reaction, except for quantitating the base of the nucleoside according to the HPLC method, the same method as in the assay of purine nucleoside phosphorylase activity is conducted.

3. Optimum pH

The same method as in the assay of purine nucleoside phosphorylase activity is conducted except for using a substrate solution prepared by dissolving a nucleoside (20 mM inosine or uridine) and 0.1M potassium dihydrogenphosphate, and adjusting to pH 4 to 10 with a diluted aqueous solution of hydrochloric acid or sodium hydroxide.

4. Stable pH

Except for using an enzyme solution incubated in a 0.2M acetate buffer (pH 3.5 to 6) and a Tris-HCl buffer pH 7 to 9) at 37° C. for 16 hours, the same method as in the assay of either purine nucleoside phosphorylase activity or pyrimidine nucleoside phosphorylase activity is conducted.

5. Optimum Temperature

Except for carrying out the reaction at the respective temperatures of 30° to 80° C., the same method as in the assay of either purine nucleoside phosphorylase activity or pyrimidine nucleoside phosphorylase activity is conducted.

6. Stable Temperature Range

Except for using an enzyme solution heated at 30° to 80° C. for 15 minutes, the same method as in the assay of either purine nucleoside phosphorylase activity or pyrimidine nucleoside phsophorylase activity is conducted.

The characteristics of the enzyme obtained from the microorganism of the present invention as described above are that it has optimum temperature and stable temperature ranges at relatively higher temperatures and also has a markedly high specific activity. Therefore, by the use of a preparation containing an enzyme having such characteristics for the production of nucleosides, the amount of the enzyme preparation to be used for the reaction can be made small, whereby the nucleosides can be prepared with good yield by the use of a small amount of enzyme. Further, since the reaction can be carried out at a relatively higher temperature (45° C. or higher), contamination with bacteria can be also prevented.

II. PRODUCTION OF NUCLEOSIDES

The production of nucleosides by the use of the enzyme preparation as described above can be practiced by carrying out in a reactor the contact reaction of a base donor, a saccharide residue donor and a phosphoric acid donor as described below with the enzyme preparation.

(1) Base Donor

The base donor to be used in the process of the present invention is a compound which can supply a base into the reaction system. The base donor to be used is selected according to the objective nucleoside, examples being heterocyclic bases and derivatives thereof capable of forming an N-glycoside bond with the saccharide moiety of the saccharide residue donor through the action of nucleoside phosphorylase. Specific examples of heterocyclic bases are purine and derivatives thereof, pyrimidine and derivatives thereof, triazole and derivatives thereof, imidazole and derivatives thereof, deazapurine and derivatives thereof, azapyrimidine and derivatives, or pyridine and derivatives thereof. As the base donor, heterocyclic bases themselves as a matter of course, and also nucleosides and nucleotides having said heterocyclic bases may be employed.

Specifically, examples are purine derivatives having substituents at 1 or more positions of the 1-position, 2-position, 6-position or 8-position of the purine base (e.g., amino group, substituted amino group, hydroxyl group, oxo group, mercapto group, acyl group, alkyl group, substituted alkyl group, alkoxyl group and halogen atom), such as adenine, guanine, hypoxanthine, xanthine, 6-mercaptopurine, 6-thioguanine, $N^6$-alkyl or acyladenine, 2-alkoxyadenine, 2-thioadenine and 2, 6-diaminopurine; pyrimidine derivatives having the same substituents as mentioned above at 1 of more positions of the 2 position, 4-position or 5-position of pyrimidine, such as cytosine, uracil, thymine, 5-halogenouracil (5-fluorouracil and 5-iodouracil), 5-halogenocytosine (5-fluorocytosine), 5-trihalogenomethyluracil (5-trifluoromethyluracil), 2-thiocytosine, 4-thiouracil, $N^4$-acylcytosine and 5-halogenovinyluracil; 1, 2, 4-triazole derivatives having a substituent at the 3-position of 1, 2, 4-triazole, such as 1, 2, 4-triazole-3-carboxamide, 1, 2, 4-triazole-3-carboxylic acid and 1, 2, 4-triazole-3-carboxylic acid alkyl ester; imidazole derivatives having substituents at the 4-position or 5-position of imidazole, such as 5-aminoimidazole-4-carboxamide, 4-carbamoylimidazolium-5-oleate and benzimidazole; deazapurine derivatives at the 1-position, 3-position or 7-position of purine, such as 1-deazadenine, 3-deazadenine, 3-deazaguanine, 7-deazadenine, 7-deazaguanine, or compounds having the same substitutes as in the above-mentioned purine derivatives; azapurine derivatives such as 8-azadenine and 7-deaza-8-azahypoxanthine (allopurinol); azapyrimidine derivatives such as 5-azathymine, 5-azacytosine and 6-azauracil; pyridine derivatives such as 3-deazauracil, nicotinic acid and nicotinic acid amide.

Saccharide Residue Donor

The saccharide residue donor is for supplying a saccharide residue into the reaction system. That is, the saccharide residue donor is selected according to the objective nucleoside, and ribose compounds and deoxyribose compounds capable of forming an N-glycosidic bond with the base moiety of the base donor through the action of nucleoside phosphorylase are examples. Examples of ribose compounds are ribonucleosides such as inosine, guanosine, uridine and ribofuranosylthymine, and ribose 1-phosphate, while examples of deoxyribose compound are deoxynucleosides such as 2'-deoxyinosine, 2'-deoxyguanosine, 2'-deoxyuridine, thymidine, 2', 3'-dideoxyinosine, 2', 3'-dideoxyguanosine, 2', 3'-dideoxyuridine and 3'-deoxythymidine, and 2-deoxyribose 1-phosphate and 2, 3-dideoxyribose 1-phosphate.

When as an enzyme preparation, a preparation other than a purified enzyme is to be used, in addition to the saccharide residue donor mentioned above, ribose compounds such as adenosine, cytidine and xanthosine, and deoxyribose compounds such as 2'-deoxyadenosine, 2'-deoxycytidine and 2'-deoxyxanthosine can be further used.

(3) Phosphoric Acid Donor

As the phosphoric acid donor, any compound dissociable into phosphate ions in the reaction mixture may be used. For example, free phosphoric acid or phosphates (e.g., alkali metal salts such as sodium and potassium, and ammonium salts) are preferably used. Also, as the phosphoric acid donor, a system capable of liberating phosphate ions in the reaction mixture, for example, combinations of various phosphoric acid ester derivatives and phosphatase, combinations of nucleotides and nucleotidase can also be utilized.

(4) Reaction Conditions

As the reaction mixture, a mixture containing a base donor, a saccharide residue donor and a phosphoric acid donor dissolved or suspended in water or a buffer is employed. By bringing the reaction mixture into contact with the enzyme preparation as described above, the nucleoside corresponding to the base donor employed is produced enzymatically.

The concentrations of the base donor, the saccharide residue donor and the phosphoric acid donor employed are suitably selected from the range of 0.1 to 500 mM.

The reaction generally proceeds well at a temperature ranging from 35° to 80° C., but particularly a reaction temperature of about 40° to 70° C. is preferred. If the reaction temperature is 35° C. or less, the reaction rate is slow and gives rise to poor reaction efficiency. On the other hand, at a reaction temperature of 80° C. or higher, there is the risk of the nucleoside phosphorylase activity being lowered.

The pH of the reaction mixture is generally maintained in the range of pH 5 to 10, preferably pH 5 to 9. When the pH changes during the reaction, it may be corrected to a preferable pH range by the use of an acid or an alkali.

After the reaction, the reaction mixture is separated from the enzyme preparation and subjected to the separation/purification step of the objective nucleoside.

The nucleoside thus formed can be separated and purified according to a known method or its modified method. For example, various chromatographies such as ion exchange chromatography, adsorption chromatography, partition chromatography and gel filtration; the methods utilizing partition between two liquid phases such as countercurrent distribution and countercurrent extraction; and the methods utilizing difference in solubility such as concentration, cooling and organic solvent addition, either alone or in a suitable combination thereof can be used.

EXAMPLES

The present invention will now be described in specific detail with respect to the following Examples and Comparative Examples.

EXAMPLE 1

Into 500 ml of a sterilized medium (pH 7.0) containing 0.5% of yeast extract (Difco), 1.0% of peptone (Difco), 0.7% of meat extract (Difco) and 0.3% of sodium chloride was inoculated *Bacillus stearothermophilus* TH6-2 (FERM BP-2758), and shaking culture was carried out at 50° C. for 18 hours.

The culture broth obtained was centrifuged, and the microorganism cells were collected and washed, and the sterilized water was added to prepare 250 ml of a cell suspension. To each 10 ml of aliquot of the cell suspension was added 10 ml of a substrate solution (pH 6.0) containing a 40 mM base donor, a 40 mM saccharide residue donor and 40 mM potassium dihydrogenphosphate, and the reaction was carried out under stirring at 40° to 60° C.

After the reaction, the amounts of various nucleosides were assayed by high performance liquid chromatography (column: YMC A-312 (manufactured by Yamamura Kagaku Kenkyusho, K.K.), eluent: 20 mM Tris-HCl buffer (pH 7.5) containing 2.5 to 5% acetonitrile, detection: absorbance at 250–260 nm).

$$\text{Formation ratio (\%)} = \frac{\text{Concentration of nucleoside formed (M)}}{\text{Concentration of base donor used (M)}} \times 100$$

The results are shown in Table 5.

TABLE 5

| Base Donor | Saccharide Residue Donor | Product | Reaction Conditions Temperature (°C.) | Time (hr) | Formation Ratio (%) (Relative to Base) |
|---|---|---|---|---|---|
| Adenine | Uridine | Adenosine | 40 | 24 | 61 |
| " | " | " | 50 | 2 | 45 |
| " | " | " | 50 | 24 | 82 |
| " | " | " | 60 | 2 | 60 |
| " | " | " | 60 | 24 | 85 |
| Adenine | 2-Deoxyuridine | 2'-Deoxyadenosine | 40 | 2 | 25 |
| " | " | " | 50 | 2 | 55 |
| " | " | " | 60 | 2 | 63 |
| " | " | " | 60 | 4 | 70 |
| " | " | " | 60 | 8 | 78 |
| " | 2',3'-Dideoxyuridine | 2',3'-Dideoxyadenosine | 55 | 24 | 15[1) |
| Thymine | Uridine | Ribofuranosylthymine | 40 | 2 | 48 |
| " | " | " | 50 | 2 | 58 |
| " | " | " | 60 | 2 | 60 |
| " | " | " | 60 | 24 | 65 |
| Thymine | 2-Deoxyuridine | Thymidine | 40 | 2 | 23 |
| " | " | " | 50 | 2 | 55 |
| " | " | " | 60 | 2 | 66 |
| " | " | " | 60 | 8 | 67 |

[1)]shown in ratio to saccharide residue donor

EXAMPLE 2

By using a substrate solution (pH 6.0) containing 20 mM allopurinol as the base donor, 30 mM uridine as the saccharide residue donor and 75 mM potassium dihydrogenphosphate, the reaction was carried out in the same manner as in Example 1 at 60° C. for 8 hours to produce a ribofuranosyl derivative of allopurinol in a yield of 95% (ratio relative to allopurinol).

EXAMPLE 3

By using a 20 mM base donor (allopurinol, benzimidazole, 6-mercaptopurine, purine, 6-thioguanine), a 30 mM saccharide residue donor (uridine, 2'-deoxyuridine) and 30 mM potassium dihydrogenphosphate, the reaction was carried out in the same manner as in Example 1 at 50° C. for 8 hours to produce ribofuranosyl derivatives or 2'-deoxyribofuranosyl derivatives bearing various base donors as the base. The results are shown in Table 6.

TABLE 6

| Base Donor | Saccharide Residue Donor | Formation Ratio (%) (Ratio Relative to Base) |
|---|---|---|
| Allopurinol | Uridine | 80 |
| " | 2'-Deoxyuridine | 97 |
| Benzimidazole | Uridine | 75 |
| " | 2'-Deoxyuridine | 86 |

TABLE 6-continued

| Base Donor | Saccharide Residue Donor | Formation Ratio (%) (Ratio Relative to Base) |
|---|---|---|
| 6-Mercaptopurine | Uridine | 50 |
| " | 2'-Deoxyuridine | 43 |
| Purine | Uridine | 94 |
| " | 2'-Deoxyuridine | 65 |
| 6-Thioguanine | Uridine | 9 |
| " | 2'-Deoxyuridine | 65 |

EXAMPLE 4

By using a substrate solution (pH 6.0) containing 40 mM 1, 2, 4-triazole-3-carboxamide (hereinafter called "triazole") as the base donor, 40 mM uridine, inosine, cytidine, adenosine or guanosine as the saccharide residue donor and 40 mM potassium dihydrogenphosphate, ribavirin was produced in the same manner as in Example 1. The results are shown in Table 7.

TABLE 7

| Saccharide Residue Donor | Reaction Conditions Temperature (°C.) | Time (hr) | Formation Ratio (%) (Ratio Relative to Triazole) |
|---|---|---|---|
| Uridine | 60 | 4 | 94.2 |
| Inosine | 67 | 48 | 83.6 |
| Cytidine | 50 | 24 | 92.9 |
| Adenosine | 67 | 24 | 72.7 |
| Guanosine | 67 | 24 | 98.4 |

Concerning cytidine and adenosine, the nucleoside phosphorylase of the present invention does not recognize them as the substrate, and therefore it may be considered that they may be converted by co-existing deaminase to uridine and inosine, respectively, which are then utilized as the substrate.

EXAMPLE 5

By using a substrate solution (pH 6.0) containing 40 mM triazole as the base donor, 60 mM inosine as the saccharide residue donor and 40 mM potassium dihydrogenphosphate, reactions were carried out in the same manner as in Example 1 at respective reaction temperature (40° to 70° C.) for 24 hours to produce ribavirin. The results are shown in Table 8.

TABLE 8

| Reaction Temperature (°C.) | 40 | 50 | 60 | 63 | 65 | 67 | 70 |
|---|---|---|---|---|---|---|---|
| Formation Ratio (%) (Ratio Relative to Triazole) | 37.0 | 58.0 | 71.7 | 73.7 | 76.0 | 78.7 | 77.9 |

EXAMPLE 6

A culture product obtained in the same manner as in Example 1 was centrifuged to obtain viable cells. Next, 2.0 g of the viable cells were suspended in 1.0 ml of a 0.1M Tris-HCl buffer (pH 7.0), and the above cell suspension was added into a separately prepared resin solution containing 0.08 g benzoin ethyl ether as a photopolymerization initiator added into 8.0 g photocurable resin (ENT-2000: Kansai Paint K.K.). After thorough mixing, the mixture was cast onto a transparent film, which was irradiated with rays at around 360 nm simultaneously on both the front and back surfaces of the film for 3 minutes to obtain a photopolymer.

From the immobilized product, a portion containing 0.2 g of cells was sampled, broken into pieces, and the above immobilized product was introduced into 10 ml of a substrate solution (pH 6.0) containing 40 mM triazole, 40 mM uridine and 60 mM potassium dihydrogenphosphate. Ribavirin was produced while stirring the mixture at 60° C. for 8 hours.

As a result of assay of the formation ratio according to the HPLC method as described above, the formation ratio of ribavirin relative to triazole was found to be 90%.

Further, when the reaction was carried out repeatedly 10 times, the formation ratio of ribavirin was maintained at 90% and no lowering in enzyme activity was observed.

EXAMPLE 7

Into the cultured product obtained similarly as described in Example 1 were added triazole, uridine or inosine, and potassium dihydrogenphosphate each to the final concentration of 40 mM, and further shaking culture was carried out at 50° C. (when using uridine) or 65° C. (when using inosine) for 24 hours. After cultivation, the centrifuged supernatant was subjected to the assay of the formation ratio of ribavirin by the HPLC method, and consequently the formation ratio of ribavirin when using uridine was found to be 91.9% in terms of the ratio relative to triazole, and 65.9% when using inosine.

EXAMPLE 8

Preparation of Purified Enzyme

Bacillus stearothermophilus TH6-2 was inoculated from a bouillon slant into a large test tube containing 10 ml of a medium adjusted to pH 7.2 containing 1.0% peptone, 0.7% meat bouillon, 0.5% yeast extract and 0.3% sodium chloride and cultured overnight at 50° C. The cultured product obtained was transferred into a flask of 300 ml volume containing 30 ml of a medium of the same composition and the same pH, cultured at 50° C. for 8 hours, and by the use of the cultured product as the seed culture, the whole amount was added into a jar fermenter of 5-liter volume containing 3 liters of the above-mentioned medium. Then cultivation was carried out under the conditions of 50° C., stirring speed of 350 r.p.m., and aeration of 1.0 v.v.m. for 18 hours. From the culture broth thus obtained, about 30 g of wet cells were obtained, which were suspended in 1.5 liters of a 50 mM Tris-HCl buffer (pH 7.2) containing 0.1% Triton X-100 (Sigma) and 5 mM EDTA. 750 mg of lysozyme (Sigma) was added, and the mixture was incubated at 37° C. for one hour. The lysis solution was centrifuged at 8,000 r.p.m., and the cell residue was removed. Thereafter the mixture was adjusted to pH 6.0 with the addition of 2N HCl and subjected to a heat treatment at 50° C. for 5 minutes, followed by centrifugation at 8,000 r.p.m. to obtain a supernatant as the crude enzyme solution.

The crude enzyme solution was fractionated according to salting out by using ammonium sulfate, and the protein precipitates at 40% to 90% saturation were dissolved in a 50 mM acetic acid-sodium acetate buffer (pH 6.0) and dialyzed overnight against a large amount of the same buffer. The internal solution obtained was centrifuged to remove the precipitates formed during dialysis. The supernatant was passed through a DEAE Toyopearl column (Toso K.K.) (2.2×60 cm) equilibrated with the above-mentioned acetate buffer (hereinafter referred to as buffer A), and the proteins adsorbed were eluted by the linear gradient method of 0 to 0.5M sodium chloride (by using buffer A), and the purine nucleoside phosphorylase fraction and the pyrimidine nucleoside phosphorylase fraction were respectively recovered. The respective active fractions were dialyzed against buffer A and column chromatographed according to the same procedures as described above by the use of 20 ml of DEAE Toyopearl resin in a 25 ml volume syringe (Terumo K.K.), and the respective active fractions were recovered. Next, these active fractions were respectively subjected to gel filtration by the use of Toyopearl HW-55S (Toso K.K.) column (2.4×80 cm) equilibrated with buffer A to recover both enzymes as substantially uniform purified preparations.

The protein amounts, the total activities and the degree of enzyme purity of the active fractions during the purification process of the both enzymes are shown in Table 9.

The degree of enzyme purity was determined according to the method in which the relative proportions of the respective bands were measured by measuring the electrophoresis pattern obtained by the SDS-polyacrylamide gel electrophoresis by means of a densitometer.

TABLE 9

| | Purine Nucleoside Phosphorylase | | | | Pyrimidine Nucleoside Phosphorylase | | | |
|---|---|---|---|---|---|---|---|---|
| Fraction Name | Protein Amount (mg) | Degree of Enzyme Purity (%) | Total Activity (U) | Specific Activity (U/mg) | Protein Amount (mg) | Purification Degree (%) | Total Activity (U) | Specific Activity (U/mg) |
| Crude enzyme solution (after heat treatment) | ① | — | 97700 | 16.1 | ① | — | 87800 | 14.4 |
| Ammonium sulfate fraction | ② | — | 79500 | 32.0 | ② | — | 81600 | 26.6 |

TABLE 9-continued

| Fraction Name | Purine Nucleoside Phosphorylase | | | | Pyrimidine Nucleoside Phosphorylase | | | |
|---|---|---|---|---|---|---|---|---|
| | Protein Amount (mg) | Degree of Enzyme Purity (%) | Total Activity (U) | Specific Activity (U/mg) | Protein Amount (mg) | Purification Degree (%) | Total Activity (U) | Specific Activity (U/mg) |
| (40-90% saturation) DEAE Toyopearl chromatography (first) | 400 | — | 66800 | 167 | 291 | — | 57500 | 198 |
| DEAE Toyopearl chromatography (second) | 109 | 74 | 40000 | 370 | 160 | 69 | 36100 | 225 |
| Toyopearl HW-55S chromatography | 74 | 93 | 34300 | 465 | 81 | 90 | 24200 | 295 |

1 Total protein amount is 6080 mg
2 Total protein amount is 3770 mg

COMPARATIVE EXAMPLE 1

From each slant of *Brevibacterium acetylicum* AT-6-7 (ATCC 39311) and *Bacillus stearothermophilus* TH6-2, the microorganism was inoculated into a large test tube containing 10 ml of a medium (containing 1% peptone, 0.7% meat extract, 0.3% sodium chloride, 0.5% yeast extract, pH 7.2), and respectively subjected to shaking culture at 28° C. (in the case of AT-6-7) and at 50° C. (in the case of TH6-2) for 18 hours, followed by centrifugal separation of the respective culture broths to separate the microorganism cells. After washing cells of the same wet weight were each suspended in 10 ml of deionized water.

Into each of the cell suspensions was added 10 ml of a substrate solution containing 0.4 mM triazole, 0.4 mM uridine and 0.4 mM potassium dihydrogenphosphate (adjusted to pH 7.0 in the case of AT-6-7, pH 6.0 in the case of TH6-2), and the reaction was carried out under stirring in a closed system at 45° C. or 65° C. Sampling was performed periodically to measure the formation ratio of ribavirin according to the HPLC method as described above.

Figure 5:
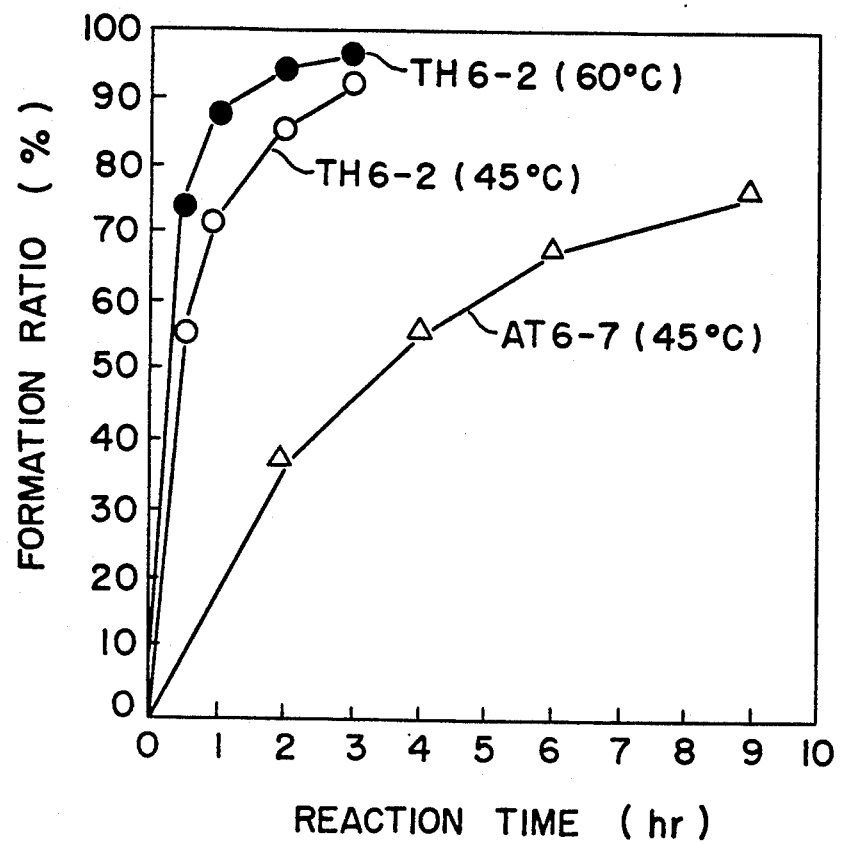
FIG. 5 is a graph indicating a comparison of the formation ratio of 1-β-D-ribofuranosyl-1, 2, 4-triazole-3-carboxamide (ribavirin) relative to the reaction time when ribavirin is produced by the use of the cells of Bacillus stearothermophilus TH6-2 or Brevibacterium acetvlicum AT-6-7 as an enzyme source.

The results are shown in FIG. 5. As is apparent from FIG. 5, when the enzyme preparation prepared from the microorganism of the present invention is used, it has been found that the objective compound can be produced in an even shorter time than AT-6-7 which was an extremely excellent enzyme preparation source, and the amount of the enzyme preparation used can be made smaller.

As described above, the enzyme preparation containing the nucleoside phosphorylase of the present invention contains a large amount of nucleoside phosphorylase having high specific activity and heat resistance, is derived from the cells of one or more kinds of microorganisms of the microorganism group belonging to thermophiles of the genus Bacillus having high nucleoside phosphorylase activity per unit cell weight, and by the use of such enzyme preparation for the production of nucleosides, a very useful method which has the following specific features and is rich in practical applicability can be provided.

(1) A large amount of nucleoside phosphorylase with high specific activity is contained in the enzyme preparation, and when it is employed in the production of nucleosides, nucleosides can be produced in a good yield with a small amount of the enzyme.

(2) Nucleoside phosphorylase with optimum temperature and stable temperature ranges in a relatively higher temperature region is contained in the enzyme preparation. For this reason, the reaction can be carried out at a high temperature, whereby deactivation of the enzyme, decomposition of the reaction product, etc. due to contamination with bacteria can be suppressed.

(3) A preparation containing both enzymes of purine nucleoside phosphorylase and pyrimidine nucleoside phosphorylase as the nucleoside phosphorylase can also be obtained. By the use of such preparation for the nucleoside production, for example, the two enzymes will act concomitantly as shown in the reaction scheme shown below, whereby nucleosides can be produced at a rate of 2-fold or more as compared with the enzyme preparation containing only one nucleoside phosphorylase.

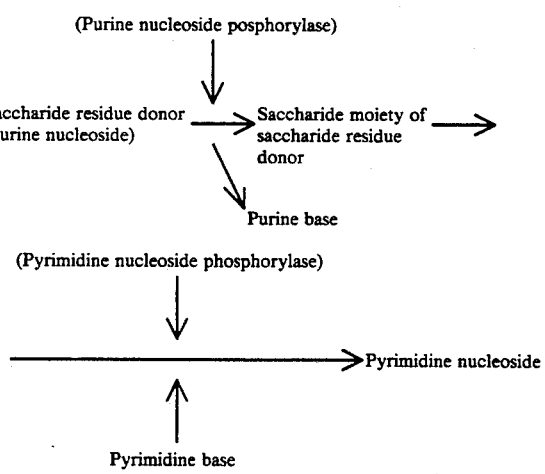

Also, the microorganism of the present invention can grow at a relatively higher temperature, resulting in a rapid growth rate, and contains a large amount of the enzymes suitable for the nucleoside production as described above in the cells obtained by cultivation. Therefore it is extremely useful as an enzyme preparation or a preparation source therefor to be used for the nucleoside production.

Further, by the use of the cultured product of the microorganism as an enzyme preparation of the present invention, autolysis of the cells can be prevented.

Also, the nucleoside phosphorylase obtained by the microorganism of the present invention as described above has specific features of high specific activity and optimum temperature and stable temperature ranges in a relatively higher temperature region, and therefore can be clearly distinguished from the known nucleoside phosphorylases. Also, by using such an enzyme for the production of nucleosides, the effects (1) and (2) as described above can be obtained. In addition, by using both of the enzymes of purine nucleoside phosphorylase and pyrimidine phosphorylase of the present invention, the above effect (3) can be exhibited.

UTILIZABILITY IN INDUSTRY

The process for producing nucleosides of the present invention uses an enzyme preparation derived from the cells of a microorganism belonging to thermophiles of the genus Bacillus containing a large amount of heat-resistant nucleoside phosphorylase having high specific activity, and having high nucleoside phosphorylase activity per unit cell weight, as an enzyme source for the production of nucleosides, and is an extremely practical method which can produce objective nucleosides in a good yield with a small amount of the enzyme.

We claim:

1. A biologically pure culture of *Bacillus stearothermophilus* TH 6-2 (FERM BP-2758).